(12) United States Patent
Chen

(10) Patent No.: US 12,076,043 B2
(45) Date of Patent: Sep. 3, 2024

(54) RENAL PUNCTURE SAMPLING DEVICE

(71) Applicant: ZHEJIANG UNIVERSITY, Hangzhou (CN)

(72) Inventor: Da Jin Chen, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 718 days.

(21) Appl. No.: 17/420,687

(22) PCT Filed: Aug. 18, 2020

(86) PCT No.: PCT/CN2020/109674
§ 371 (c)(1),
(2) Date: Jul. 5, 2021

(87) PCT Pub. No.: WO2022/027729
PCT Pub. Date: Feb. 10, 2022

(65) Prior Publication Data
US 2022/0218387 A1 Jul. 14, 2022

(30) Foreign Application Priority Data
Aug. 7, 2020 (CN) .......................... 202010786155.8

(51) Int. Cl.
*A61B 17/34* (2006.01)
*A61B 10/02* (2006.01)
*A61B 17/00* (2006.01)

(52) U.S. Cl.
CPC ...... *A61B 17/3403* (2013.01); *A61B 10/0233* (2013.01); *A61B 10/0283* (2013.01); *A61B 2017/00544* (2013.01)

(58) Field of Classification Search
CPC ............ A61B 17/3403; A61B 10/0233; A61B 10/0283; A61B 2017/00544;
(Continued)

(56) References Cited

U.S. PATENT DOCUMENTS

| 2017/0000520 A1* | 1/2017 | Shepherd | A61B 17/3403 |
| 2018/0132833 A1* | 5/2018 | Gotlib | A61B 34/25 |

FOREIGN PATENT DOCUMENTS

| CN | 209984268 U | * 1/2020 | ............. A61B 17/34 |

OTHER PUBLICATIONS

English-language machine translation of CN-209984268-U (Year: 2024).*

* cited by examiner

*Primary Examiner* — Andrey Shostak
(74) *Attorney, Agent, or Firm* — Bayramoglu Law Offices LLC

(57) ABSTRACT

A renal puncture sampling device includes a base, a sampler, a first pneumatic cylinder, a support frame, a second pneumatic cylinder, and a controller. The sampler includes a sample storage cylinder, a puncture needle, and a piston. The puncture needle is fixed at a left side of the sample storage cylinder; the piston is located in an inner cavity of the sample storage cylinder, and a piston rod passes through a right sidewall of the sample storage cylinder; an end of a telescopic rod of the first pneumatic cylinder is connected to the piston rod; the second pneumatic cylinder drives the support frame to horizontally move left and right; a first position sensor is disposed on an inner wall of a left end of a puncture channel of the puncture needle; a second position sensor is disposed at a center of a left end of the support frame.

10 Claims, 1 Drawing Sheet

(58) Field of Classification Search
CPC .... A61B 2017/3409; A61B 2017/3413; A61B 17/3421
See application file for complete search history.

RENAL PUNCTURE SAMPLING DEVICE

CROSS REFERENCE TO THE RELATED APPLICATIONS

This application is the national phase entry of International Application No. PCT/CN2020/109674, filed on Aug. 18, 2020, which is based upon and claims priority to Chinese Patent Application No. 202010786155.8, filed on Aug. 7, 2020, the entire contents of which are incorporated herein by reference.

TECHNICAL FIELD

The present invention relates to the technical field of medical appliances, and in particular to the technical field of a renal puncture sampling device.

BACKGROUND

Renal puncture is also known as renal biopsy or renal puncture biopsy. Kidney diseases come in various types, with complicated etiology and pathogenesis. Therefore, the clinical manifestations of many kidney diseases are not completely consistent with the histopathological changes of kidneys. For example, when the clinical manifestations indicate nephrotic syndrome (NS), there may be various pathological changes such as minimal pathological changes, minor pathological changes, mild mesangial hyperplasia, membranous nephropathy (MN), membranoproliferative glomerulonephritis (MPGN), or focal segmental glomerulosclerosis (FSGS), which vary considerably in the treatment plan and disease progression result. A kidney disease also manifests different histopathological changes in different developmental stages. For example, immunoglobulin A (IgA) nephropathy may have pathological manifestations including almost all developmental stages, from a developmental stage in which the kidney tissue is nearly normal to a developmental stage in which most glomeruli become sclerosis. Therefore, the understanding of histomorphological changes of kidneys provides an important basis for clinicians to judge the progression of a disease, treat the disease, and estimate the prognosis. Admittedly, the development of renal pathological examination marks a leap forward for the development of nephrology. Renal pathological examination results have become gold indicators for the diagnosis of kidney diseases. With renal puncture biopsy, the clinical diagnosis of more than one-third of patients can be corrected.

At present, renal puncture procedures are conducted typically by using disposable automatic ejection biopsy guns (where 18G or 16G biopsy needles for adults and 18G biopsy needles for children). In this case, needle guidance and biopsy are both conducted by sonographers, and a nephrologist will conduct biopsy under the ultrasound guidance performed by a sonologist. Generally, a guiding device with ultrasound is used to increase the biopsy accuracy. However, this method is difficult to accurately determine the puncture location, and thus cannot adjust the puncture location according to a specific patient.

SUMMARY

The present invention is intended to solve the problems in the prior art and provide a renal puncture sampling device that can be automatically adjusted to meet the puncture needs of patients with different ages and body weights.

In order to achieve the above objectives, the present invention provides a renal puncture sampling device, including a base, a sampler, a first pneumatic cylinder, a support frame, a second pneumatic cylinder, and a controller. The sampler includes a sample storage cylinder, a puncture needle, and a piston. The puncture needle is fixed at a left side of the sample storage cylinder; the piston is located in an inner cavity of the sample storage cylinder, and a piston rod passes through a right sidewall of the sample storage cylinder; an end of a telescopic rod of the first pneumatic cylinder is connected to the piston rod; the sampler and the first pneumatic cylinder are separately fixed at a center of a top surface of the support frame; the second pneumatic cylinder is fixed at a right side of a top surface of the base and drives the support frame to horizontally move left and right; a first position sensor is disposed on an inner wall of a left end of a puncture channel of the puncture needle to determine a first real-time position $W_1$; a second position sensor is disposed at a center of a left end of the support frame to determine a second real-time position $W_2$; a first angle sensor and a second angle sensor are symmetrically disposed at a front side and a back side of the left end of the support frame respectively to determine a first real-time included angle A between the first angle sensor and a central line of the puncture channel and a second real-time included angle B between the second angle sensor and the central line of the puncture channel; a liquid level sensor is disposed inside the sample storage cylinder; the controller is electrically connected to the sampler, the first pneumatic cylinder, the support frame, and the second pneumatic cylinder, respectively; and the controller determines a corresponding specific puncture needle insertion length D, a specific maximum puncture needle angle deviation C, and specific sampling volume information Q according to input specific age information E and specific body weight information M of a specific patient, and then controls actions of the first pneumatic cylinder and the second pneumatic cylinder through a prebuilt specific sampling matrix F (E, M, D, C, Q).

Preferably, a sample outlet and a scale may be disposed on an outer wall of the sample storage cylinder; and a flared column may be disposed at a left end of the sample storage cylinder, and a soft pad may be disposed at a left side of the flared column.

Preferably, the support frame may include a straight rod body, a bent rod body, and inclined rod bodies; the straight rod body may be located at a right side of the bent rod body; an arc center of the bent rod body may be located at the right side of the bent rod body; a front end and a back end of the straight rod body may be connected respectively to a front end and a back end of the bent rod body through the inclined rod bodies; and the second position sensor, the first angle sensor, and the second angle sensor may be fixed on the bent rod body separately.

Preferably, the support frame may further include a reinforcing rod; the reinforcing rod may be located between the straight rod body and the bent rod body, and a front end and a back end of the reinforcing rod may be fixed to the inclined rod bodies, respectively; a plurality of slide rails may be horizontally disposed left and right on a top surface of the base; and a slide block may be slidably disposed on each of the slide rails, and a top end of the slide block may be connected to the reinforcing rod.

Preferably, a standard sampling matrix $F_0$ ($E_0$, $M_0$, $D_0$, $C_0$, $Q_0$) may be set in the controller, where $E_0$ represents standard age information, $M_0$ represents standard body weight information, and $D_0$, $C_0$, and $Q_0$ are a standard puncture needle insertion length, a maximum standard puncture needle angle deviation, and standard sampling volume information corresponding to $E_0$ and $M_0$, respectively.

Preferably, the specific puncture needle insertion length D may be calculated according to the following formula:

$$D = \left[\left(1 - \frac{|E - E_0|}{E_0}\right) + \left(\frac{|M_0 - M|}{M_0}\right)\right] \times D_0.$$

Preferably, the specific sampling volume information Q may be calculated according to the following formula:

$$Q = \left[\left(1 - \frac{|E - E_0|}{E_0}\right) + \left(1 - \frac{|M_0 - M|}{M_0}\right)\right] \times Q_0.$$

Preferably, when the puncture needle is at an initial position, if $|A_1-B_1|=0$, the puncture needle may be in a standard insertion state;

when the puncture needle is at the initial position, if $|A_1-B_1|>0$, the puncture needle has a certain angle deviation during insertion;

the specific maximum puncture needle angle deviation C may be calculated according to the following formula:
when $D>D_0$, $$C = |A_1 - B_1| \times \left(1 - \frac{|D - D_0|}{D_0}\right) + |A_1 - B_1| \times \left(1 - \frac{|Q - Q_0|}{Q_0}\right),$$

and
when $D<D_0$, $$C = |A_1 - B_1| \times \left(1 + \frac{|D - D_0|}{D_0}\right) + |A_1 - B_1| \times \left(1 - \frac{|Q - Q_0|}{Q_0}\right);$$

where $|A_1-B_1|$ represents an initial angle deviation, and $A_1$ and $B_1$ represent a first initial included angle between the first angle sensor and the central line of the puncture channel and a second initial included angle between the second angle sensor and the central line of the puncture channel at an initial position, respectively.

Preferably, when the second pneumatic cylinder drives the sampler and the support frame to move towards the left until the first position sensor has a distance of $W_{11}$ from a patient and the second position sensor has a distance of $W_{12}$ from the patient, the sampling device may be at the initial position.

Preferably, during a puncture of the puncture needle, if $|A-B|>C$, the second pneumatic cylinder may drive the support frame and the puncture needle to return to the initial position, and sampling is stopped; and after an angle of the puncture needle is adjusted, sampling may be restarted;

during a puncture of the puncture needle, if $|A-B|<C$, the first pneumatic cylinder may pull the piston to sample until there is a sample volume of Q in the sample storage cylinder;

where $|A-B|$ is a real-time angle deviation.

Beneficial effects of the present invention include the following: a specific puncture needle insertion length D, a specific maximum puncture needle angle deviation C, and specific sampling volume information Q can be automatically adjusted according to specific conditions of patients with different ages and body weights, such as to adapt to the puncture needs of different patients. A scale is disposed on an outer wall of the sample storage cylinder, such that sampling conditions can be clearly observed. A flared column with a soft pad is disposed at a left end of the sample storage cylinder to enable the comfort of a patient in contact with the device.

The features and advantages of the present invention are described in detail through examples with reference to accompanying drawings.

In the figures: 1 represents a base, 11 represents a slide rail, 12 represents a slide block, 2 represents a sampler, 21 represents a sample storage cylinder, 211 represents a sample outlet, 212 represents a liquid level sensor, 213 represents a scale, 214 represents a flared column, 215 represents a soft pad, 22 represents a puncture needle, 221 represents a puncture channel, 222 represents a first position sensor, 23 represents a piston, 231 represents a piston rod, 3 represents a first pneumatic cylinder, 4 represents a support frame, 41 represents a straight rod body, 42 represents a bent rod body, 421 represents a second position sensor, 422 represents a first angle sensor, 423 represents a second angle sensor, 43 represents an inclined rod body, 44 represents a reinforcing rod, 5 represents a second pneumatic cylinder, and 6 represents a controller.

DETAILED DESCRIPTION OF THE EMBODIMENTS

Figure 1:
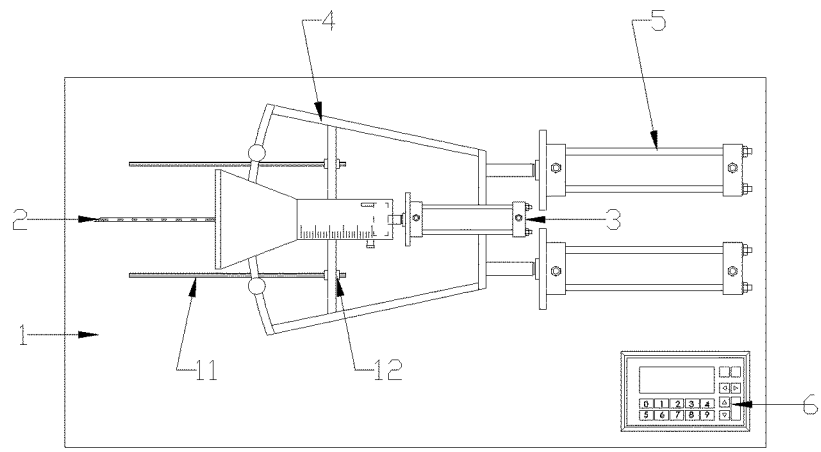
FIG. 1 is a top view of the renal puncture sampling device of the present invention.
Figure 2:
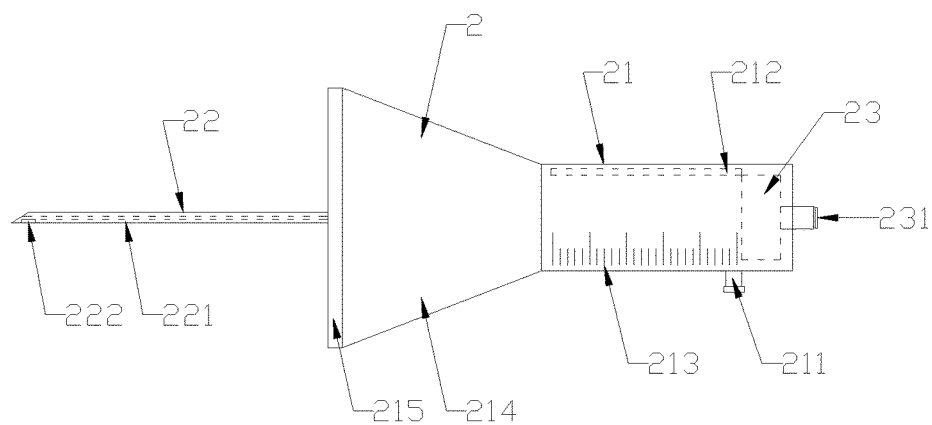
FIG. 2 is a top view of a sampler of the renal puncture sampling device of the present invention.
Figure 3:
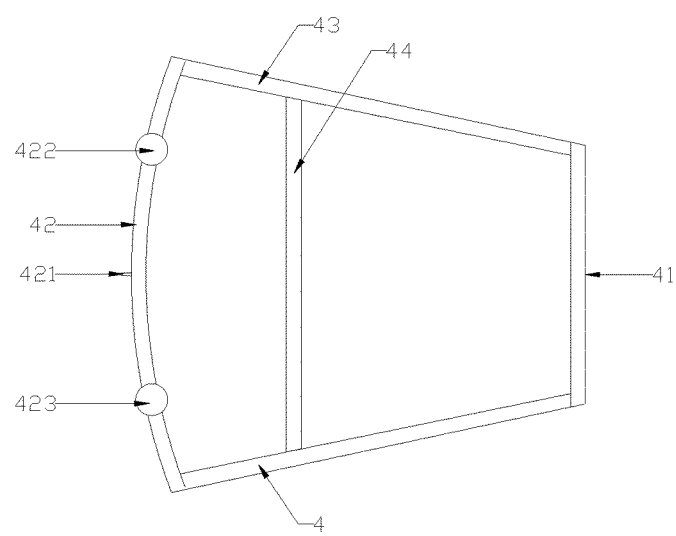
FIG. 3 is a top view of a support frame of the renal puncture sampling device of the present invention.

As shown in FIG. 1, FIG. 2, and FIG. 3, the present invention provides a renal puncture sampling device, including a base 1, a sampler 2, a first pneumatic cylinder 3, a support frame 4, a second pneumatic cylinder 5, and a controller 6. The sampler 2 includes a sample storage cylinder 21, a puncture needle 22, and a piston 23. The puncture needle 22 is fixed at a left side of the sample storage cylinder 21; the piston 23 is located in an inner cavity of the sample storage cylinder 21, and a piston rod 231 passes through a right sidewall of the sample storage cylinder 21; an end of a telescopic rod of the first pneumatic cylinder 3 is connected to the piston rod 231; the sampler 2 and the first pneumatic cylinder 3 are separately fixed at a center of a top surface of the support frame 4; the second pneumatic cylinder 5 is fixed at a right side of a top surface of the base 1 and drives the support frame 4 to horizontally move left and right; a first position sensor 222 is disposed on an inner wall of a left end of a puncture channel 221 of the puncture needle 22 to determine a first real-time position $W_1$; a second position sensor 421 is disposed at a center of a left end of the support frame 4 to determine a second real-time position $W_2$; a first angle sensor 422 and a second angle sensor 423 are symmetrically disposed at a front side and a back side of the left end of the support frame 4 respectively to determine a first real-time included angle A between the first angle sensor 422 and a central line of the puncture channel 221 and a second real-time included angle B between the second angle sensor 423 and the central line of the puncture channel 221; a liquid level sensor 212 is disposed inside the sample storage cylinder 21; the controller 6 is electrically connected to the sampler 2, the first pneumatic cylinder 3, the support frame 4, and the second pneumatic cylinder 5, respectively; and the controller 6 determines a corresponding specific puncture needle insertion length D, a specific maximum puncture needle angle deviation C, and specific sampling volume information Q according to input specific age information E and specific body weight information M of a specific patient, and then controls actions of the first pneumatic cylinder 3 and the second pneumatic cylinder 5 through a prebuilt specific sampling matrix F (E, M, D, C, Q).

A sample outlet 211 and a scale 213 may be disposed on an outer wall of the sample storage cylinder 21; and a flared column 214 may be disposed at a left end of the sample storage cylinder 21, and a soft pad 215 may be disposed at a left side of the flared column 214.

The support frame 4 may include a straight rod body 41, a bent rod body 42, and inclined rod bodies 43; the straight rod body 41 may be located at a right side of the bent rod body 42; an arc center of the bent rod body 42 may be located at the right side of the bent rod body 42; a front end and a back end of the straight rod body 41 may be connected respectively to a front end and a back end of the bent rod body 42 through the inclined rod bodies 43; and the second position sensor 421, the first angle sensor 422, and the second angle sensor 423 may be fixed on the bent rod body 42 separately.

The support frame 4 may further include a reinforcing rod 44; the reinforcing rod 44 may be located between the straight rod body 41 and the bent rod body 42, and a front end and a back end of the reinforcing rod may be fixed to the inclined rod bodies 43, respectively; a plurality of slide rails 11 may be horizontally disposed left and right on a top surface of the base 1; and a slide block 12 may be slidably disposed on each of the slide rails 11, and a top end of the slide block 12 may be connected to the reinforcing rod 44.

During a working process, the second pneumatic cylinder 5 pushes the support frame 4 to move towards the left along the slide rail 11, which drives the sampler 2 located on the support frame 4 to move towards the left, such that the puncture needle 22 is gradually inserted into a patient's body and stays at a preset position. Subsequently, the first pneumatic cylinder 3 pulls the piston 23 to move towards the right, thereby sucking a sample into the sample storage cylinder 21. After the sample suction is completed, the second pneumatic cylinder 5 drives the support frame 4 and the sampler 2 to return to the original position. The medical staff can take out the sample through the sample outlet 211.

A standard sampling matrix $F_0$ ($E_0$, $M_0$, $D_0$, $C_0$, $Q_0$) may be set in the controller 6, where $E_0$ represents standard age information, $M_0$ represents standard body weight information, and $D_0$, $C_0$, and $Q_0$ are a standard puncture needle insertion length, a maximum standard puncture needle angle deviation, and standard sampling volume information corresponding to $E_0$ and $M_0$, respectively.

The specific puncture needle insertion length D and the specific sampling volume information Q are determined according to the specific age information E and specific body weight information M of a patient.

The specific puncture needle insertion length D may be calculated according to the following formula:

$$D = \left[\left(1 - \frac{|E - E_0|}{E_0}\right) + \left(\frac{|M_0 - M|}{M_0}\right)\right] \times D_0$$

The standard age information $E_0$ represents an intermediate age, such as an age of 30 to 40. When the specific age information E of a patient is too large or too small, that is, when the patient is an elderly or a child, $|E-E_0|$ is large, and a small specific puncture needle insertion length D is selected, which can avoid harm to the human body.

The standard body weight information $M_0$ is set to a small value. If the specific weight information M of a patient is large, $|M-M_0|$ is large, and a large specific puncture needle insertion length D is selected to ensure the full suction of a sample; otherwise, a small puncture needle insertion length D is selected to avoid damage to the human body.

The specific sampling volume information Q may be calculated according to the following formula:

$$Q = \left[\left(1 - \frac{|E - E_0|}{E_0}\right) + \left(1 - \frac{|M_0 - M|}{M_0}\right)\right] \times Q_0$$

When a patient is an elderly or a child ($|E-E_0|$ is large) or when a patient has a large or small body weight ($|M_0-M|$ is large), small specific sampling volume information Q is selected to avoid harm to the human body; and on the contrary, when $|E-E_0|$ or $|M_0-M|$ is small, large sampling volume information Q is selected, such that the optimal sampling volume can be adopted for patients with different ages and body weights.

When the puncture needle 22 is at an initial position, if $|A_1-B_1|=0$, the puncture needle 22 is in a standard insertion state.

When the puncture needle 22 is at the initial position, if $|A-B_1|>0$, the puncture needle 22 has a certain angle deviation during insertion.

The specific maximum puncture needle angle deviation C may be calculated according to the following formula:

When $D>D_0$, $$C = |A_1 - B_1| \times \left(1 + \frac{|D - D_0|}{D_0}\right) + |A_1 - B_1| \times \left(1 - \frac{|Q - Q_0|}{Q_0}\right).$$

When the specific puncture needle insertion length D is large, the specific maximum puncture needle angle deviation C needs to be reduced, such that excessive deviation is avoided when the puncture needle 22 is inserted too long, which may cause damage to the human body. Moreover, when the specific sampling volume information Q is large, the specific maximum puncture needle angle deviation should also be reduced, such that the puncture needle 22 can aim at the optimal position as accurately as possible.

$$C = |A_1 - B_1| \times \left(1 + \frac{|D - D_0|}{D_0}\right) + |A_1 - B_1| \times \left(1 - \frac{|Q - Q_0|}{Q_0}\right).$$

When $D<D_0$,

When the specific puncture needle insertion length D is small, the specific maximum puncture needle angle deviation C is allowed to increase appropriately to provide a large adjustment space.

$|A_1-B_1|$ represents an initial angle deviation, and $A_1$ and $B_1$ represent a first initial included angle between the first angle sensor 422 and the central line of the puncture channel 221 and a second initial included angle between the second angle sensor 423 and the central line of the puncture channel 221 at an initial position, respectively.

When the second pneumatic cylinder 5 drives the sampler 2 and the support frame 4 to move towards the left until the first position sensor 222 has a distance of $W_{11}$ from a patient and the second position sensor 421 has a distance of $W_{12}$ from the patient, the sampling device may be at the initial position.

During a puncture of the puncture needle 22, if |A−B|>C, the second pneumatic cylinder 5 drives the support frame 4 and the puncture needle 22 to return to the initial position, and sampling is stopped; and after an angle of the puncture needle 22 is adjusted, sampling is restarted. If |A−B|<C, the first pneumatic cylinder 3 pulls the piston 23 to sample until there is a sample volume of Q in the sample storage cylinder 21. |A−B| is a real-time angle deviation.

The above examples are provided to illustrate the present invention, but not to limit the present invention. Any solution obtained by making a simple modification to the present invention shall fall within the protection scope of the present invention.

What is claimed is:

1. A renal puncture sampling device, comprising
a base, a sampler, a first pneumatic cylinder, a support frame, a second pneumatic cylinder, and a controller, wherein
the sampler comprises a sample storage cylinder, a puncture needle, and a piston;
the puncture needle is fixed at a left side of the sample storage cylinder;
the piston is located in an inner cavity of the sample storage cylinder, and a piston rod passes through a right sidewall of the sample storage cylinder;
an end of a telescopic rod of the first pneumatic cylinder is connected to the piston rod;
the sampler and the first pneumatic cylinder are separately fixed at a center of a top surface of the support frame;
the second pneumatic cylinder is fixed at a right side of a top surface of the base and the second pneumatic cylinder drives the support frame to horizontally move left and right;
a first position sensor is disposed on an inner wall of a left end of a puncture channel of the puncture needle to determine a first real-time position;
a second position sensor is disposed at a center of a left end of the support frame to determine a second real-time position;
a first angle sensor and a second angle sensor are symmetrically disposed at a front side and a back side of the left end of the support frame respectively to determine a first real-time included angle between the first angle sensor and a central line of the puncture channel and a second real-time included angle between the second angle sensor and the central line of the puncture channel;
a liquid level sensor is disposed inside the sample storage cylinder;
the controller is electrically connected to the sampler, the first pneumatic cylinder, the support frame, and the second pneumatic cylinder, respectively; and
the controller determines a specific puncture needle insertion length D, a specific maximum puncture needle angle deviation C, and specific sampling volume information Q according to input specific age information E and specific body weight information M of a specific patient, and then the controller controls actions of the first pneumatic cylinder and the second pneumatic cylinder through a prebuilt sampling matrix F (E, M, D, C, Q).

2. The renal puncture sampling device according to claim 1, wherein
a sample outlet and a scale are disposed on an outer wall of the sample storage cylinder; and
a flared column is disposed at a left end of the sample storage cylinder, and a pad is disposed at a left side of the flared column.

3. The renal puncture sampling device according to claim 1, wherein
the support frame comprises a straight rod body, a bent rod body, and inclined rod bodies;
the straight rod body is located at a right side of the bent rod body;
an arc center of the bent rod body is located at a left side of the bent rod body;
a front end and a back end of the straight rod body are connected to a front end and a back end of the bent rod body through the inclined rod bodies, respectively; and
the second position sensor, the first angle sensor, and the second angle sensor are fixed on the bent rod body separately.

4. The renal puncture sampling device according to claim 3, wherein
the support frame further comprises a reinforcing rod;
the reinforcing rod is located between the straight rod body and the bent rod body;
a front end and a back end of the reinforcing rod are fixed to the inclined rod bodies, respectively;
a plurality of slide rails are horizontally disposed left and right on the top surface of the base; and
a slide block is slidably disposed on each of the plurality of slide rails, and a top end of the slide block is connected to the reinforcing rod.

5. The renal puncture sampling device according to claim 1, wherein
a standard sampling matrix $F_0$ ($E_0$, $M_0$, $D_0$, $C_0$, $Q_0$) is set in the controller, wherein $E_0$ represents standard age information, $M_0$ represents standard body weight information, and $D_0$, $C_0$, and $Q_0$ are a standard puncture needle insertion length, a maximum standard puncture needle angle deviation, and standard sampling volume information corresponding to $E_0$ and $M_0$, respectively.

6. The renal puncture sampling device according to claim 5, wherein
the specific puncture needle insertion length D is calculated according to the following formula:

$$D = \left[\left(1 - \frac{|E-E_0|}{E_0}\right) + \left(\frac{|M_0-M|}{M_0}\right)\right] \times D_0.$$

7. The renal puncture sampling device according to claim 6, wherein
the specific sampling volume information Q is calculated according to the following formula:

$$Q = \left[\left(1 - \frac{|E-E_0|}{E_0}\right) + \left(1 - \frac{|M_0-M|}{M_0}\right)\right] \times Q_0.$$

8. The renal puncture sampling device according to claim 7, wherein when the puncture needle is at an initial position, if $|A_1-B_1|=0$, then the puncture needle is in a standard insertion state;

when the puncture needle is at the initial position, if $|A_1-B_1|>0$, then the puncture needle has an angle deviation during an insertion;

the specific maximum puncture needle angle deviation C is calculated according to the following formula:

when $D>D_0$, $$C = |A_1 - B_1| \times \left(1 + \frac{|D - D_0|}{D_0}\right) + |A_1 - B_1| \times \left(1 - \frac{|Q - Q_0|}{Q_0}\right),$$

and when $D<D_0$, $$C = |A_1 - B_1| \times \left(1 + \frac{|D - D_0|}{D_0}\right) + |A_1 - B_1| \times \left(1 - \frac{|Q - Q_0|}{Q_0}\right);$$

wherein $|A_1-B_1|$ represents an initial angle deviation, and $A_1$ and $B_1$ represent a first initial included angle between the first angle sensor and the central line of the puncture channel and a second initial included angle between the second angle sensor and the central line of the puncture channel when the puncture needle is at the initial position, respectively.

9. The renal puncture sampling device according to claim 8, wherein when the second pneumatic cylinder drives the sampler and the support frame to move left until the first position sensor has a first distance from the specific patient and the second position sensor has a second distance from the specific patient, the sampling device is at the initial position.

10. The renal puncture sampling device according to claim 9, wherein during a puncture of the puncture needle, if $|A-B|>C$, then the second pneumatic cylinder drives the support frame and the puncture needle to return to the initial position, and sampling is stopped; and after an angle of the puncture needle is adjusted, the sampling is restarted;

during the puncture of the puncture needle, if $|A-B|<C$, then the first pneumatic cylinder pulls the piston to sample until there is a sample volume of Q in the sample storage cylinder;

wherein $|A-B|$ is a real-time angle deviation.

* * * * *